United States Patent
Gauthier

(10) Patent No.: US 8,418,537 B1
(45) Date of Patent: Apr. 16, 2013

(54) DEVICE AND METHOD FOR DETECTING THE PRESENCE OF CORROSIVE MATERIAL IN DRYWALL

(75) Inventor: Thomas D. Gauthier, Lakeland, FL (US)

(73) Assignee: Environ International Corp., Tampa, FL (US)

( * ) Notice: Subject to any disclaimer, the term of this patent is extended or adjusted under 35 U.S.C. 154(b) by 596 days.

(21) Appl. No.: 12/567,358

(22) Filed: Sep. 25, 2009

(51) Int. Cl.
*G01N 17/00* (2006.01)

(52) U.S. Cl.
USPC ............. 73/86; 116/206; 411/923; 422/53; 422/400; 436/6

(58) Field of Classification Search ........ 73/86; 116/206; 422/53, 400; 436/6; 411/923
See application file for complete search history.

(56) References Cited

U.S. PATENT DOCUMENTS

| | | | |
|---|---|---|---|
| 7,451,568 B2 * | 11/2008 | Hoshall | 43/132.1 |
| 7,758,836 B1 * | 7/2010 | Huggins et al. | 423/220 |
| 2004/0184954 A1 * | 9/2004 | Guo et al. | 422/56 |
| 2010/0229497 A1 * | 9/2010 | Boisselle et al. | 52/741.3 |
| 2011/0185900 A1 * | 8/2011 | Mulholland | 95/92 |

OTHER PUBLICATIONS

Center for Toxicology & Environmental Health, LLC, Test Kit Procedures [brochure], 2009, Sunshine Co., Matlacha, FL 33993, 1 page.*
www.caslab.com/Chinese-Drywall-Testing (searched on Dec. 17, 2011).*
Center for Toxicology & Enviromental Health L.L.C.—Test Kit Procedures.*
Untitled photograph of prototype silver pins following 72 hour equilibration in defective Chinese wallboard, 2009, ENVIRON International Corp., Tampa, FL 33610, 1 page.
Untitled photograph of prototype silver pins following 72 hour equilibration in domestic wallboard, 2009, ENVIRON International Corp., Tampa, FL 33610, 1 page.
"Analysis of Corrosion on Metal Wire Pieces, Project No. G1941", Sep. 21, 2009, Materials Analysis Group, Inc., Norcross, GA 30092-4207, pp. 1-4.

* cited by examiner

*Primary Examiner* — Hezron E Williams
*Assistant Examiner* — Hoang Nguyen
(74) *Attorney, Agent, or Firm* — Drinker Biddle & Reath LLP

(57) ABSTRACT

A method for detecting the presence of corrosive material in drywall utilizing a testing device having a metal pin for insertion in the drywall, where the pin forms a visible layer when it reacts with corrosive materials in the drywall.

18 Claims, 3 Drawing Sheets

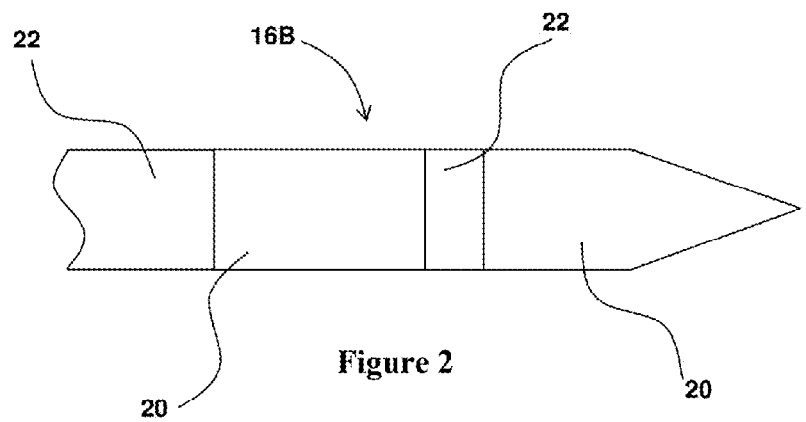
Figure 2
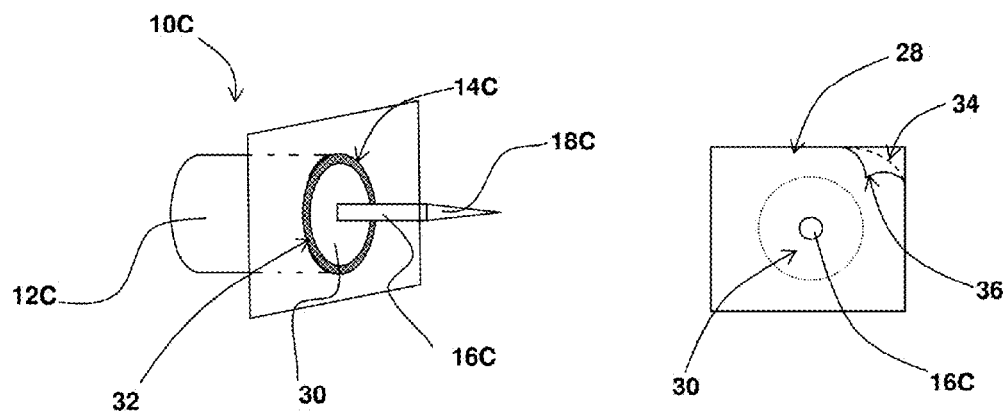
Figure 3A
Figure 3B

DEVICE AND METHOD FOR DETECTING THE PRESENCE OF CORROSIVE MATERIAL IN DRYWALL

FIELD OF THE INVENTION

This invention pertains to a device and method for detecting the presence of corrosive material including particularly $H_2S$ and OCS in drywall.

BACKGROUND OF THE INVENTION

Drywall is a common building material comprising a core of gypsum located between two cover sheets. Drywall has been used globally in the construction of interior walls and ceilings for many years and is present in substantial quantities in most modern homes throughout the world. It is therefore essential that drywall not pose environmental problems.

In 2006 an estimated 300 to 500 million pounds of drywall manufactured in China ("Chinese Drywall") were imported into the United States in part due to increased demand caused by rebuilding efforts following the active hurricane seasons in 2004 and 2005. Soon after, the US Consumer Product Safety Commission began receiving complaints from residents of newly dry-walled structures in more than 20 states that the Chinese Drywall was causing unpleasant sulfurous odors and premature HVAC system failures. The HVAC system failures were from premature corrosion of copper coil assemblies and other metal components. Much or all of the installed defective Chinese Drywall, which is apparently the source of the corrosion, may have to be removed to abate these problems. In order to contain this massive undertaking and to control its economic costs, it is important to be able to easily and accurately identify the problematic drywall which may need to be removed.

The corrosion product observed on failed or failing HVAC copper coil assemblies varies from a black discoloration to a loosely adhered black scale. The darkened surface scale has been determined by energy dispersive x-ray analysis to consist of a material containing copper, sulfur and oxygen in varying proportions, consistent with corrosion of the copper caused by exposure to hydrogen sulfide ($H_2S$) gas. In the presence of $H_2S$, copper reacts to form a mixture of copper sulfide ($Cu_2S$) and copper oxides ($Cu_2O$ and $CuO$) which correspond to the black discoloration and loosely adhered black scale.

Low concentrations of $H_2S$ have been detected in closed chamber testing of defective Chinese Drywall and higher levels are observed when the defective drywall is crushed into finer particles. Gaseous carbonyl sulfide (OCS) and carbon disulfide ($CS_2$) have also been detected in closed chamber testing of defective Chinese Drywall. In the presence of moisture, OCS hydrolyzes to form $H_2S$ and OCS is reported to corrode copper at a rate similar to the rate of corrosion caused by $H_2S$. The source of these sulfur gases is believed to be particles of elemental sulfur, possibly originally present in the mined gypsum mineral, and retained in defective Chinese Drywall as an impurity.

Existing methods for identifying defective Chinese Drywall involve destructive testing of the drywall. For example, multiple samples are cut from various locations in the suspected drywall installation and submitted to a laboratory for determination of the presence of elemental sulfur or testing in a closed chamber in the presence of copper. The determination of the presence of elemental sulfur may be performed by high performance liquid chromatography, mass spectrometry, or Fourier transform infrared analysis.

Therefore, if a device and method were provided for detecting the presence of $H_2S$, OCS, or other corrosive materials in drywall simply, inexpensively and with relative dispatch, an important contribution to the art would be a hand. If the device and method could be used on already installed drywall without removing or cutting test samples from the drywall, a particularly important contribution to the art would be a hand. Finally, if the device and method could be made tamperproof to insure that reliable results are obtained in a simple and economic way, the problem of reliably and non-destructively identifying defective Chinese Drywall and drywall containing other corrosive materials, would be solved. The present invention meets all of these objectives.

BRIEF SUMMARY OF THE INVENTION

The invention comprises a method for detecting the presence of corrosive material, including particularly $H_2S$ and OCS, in drywall having a gypsum core. The method entails providing a testing device with a handle and a pin projecting from the handle where the pin is made of a metal that forms a visible layer or scale when it reacts with the corrosive materials. The pin of the device is pressed into the core of the drywall to be tested and left in place a sufficient period to produce a visible layer indicative of the presence of a detectable amount of corrosive material. Then, the testing device is removed and the pin inspected to determine whether a corrosive material is present in the core of the drywall.

The testing device may have a single pin or a plurality of pins. Preferably, the pins will have sharpened tips. Also, a wire instead of rigid pin may be used so long as a hole for receiving the wire is first formed in the drywall.

The pin of the testing device should comprise a reactive metal chosen from the group consisting of silver, copper, gold, or alloys of silver, copper or gold. The pins may be comprised entirely of the reactive metal or they may be plated with the reactive metal. Also, selected portions of the pin may be made of or plated with reactive metals.

The distal face of the handle may be convex to establish a portion which does not enter the drywall when the pin is pressed into place for testing the drywall.

Finally, a security seal may be provided at the distal face of the handle. The seal will include a frangible central member which may be made of, for example, cardboard that will tear or separate when the testing device is removed from its installed location.

BRIEF DESCRIPTION OF THE DRAWINGS

In order to aid in understanding the invention, it will now be described in connection with exemplary embodiments thereof with reference to the accompanying drawings in which like numerical designations will be given to like features with reference to the accompanying drawings wherein:

FIG. 2 is a partial elevation view of a portion of an alternate pin design for the testing device of FIG. 1-1B;

FIG. 3A is a perspective view of yet another alternate embodiment of the testing device of invention in which the handle of the testing device is provided with a frangible member;

FIG. 3B is a front elevation view of the frangible member of FIG. 3A; and

DETAILED DESCRIPTION OF THE INVENTION

The embodiments of the invention described in detail below are not intended to be exhaustive or to limit the invention to the precise structures and operations disclosed. Rather, the described embodiments have been chosen and described to explain the principles of the invention and its application, operation and use in order to best enable others skilled in the art to follow its teachings.

Figure 1:
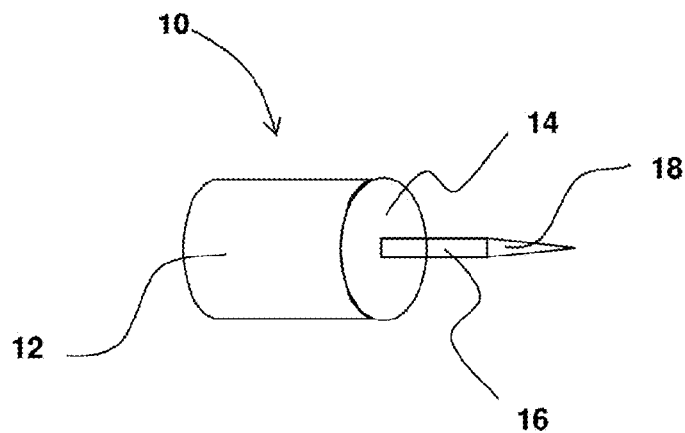
FIG. 1 is a perspective view of a testing device in accordance with the present invention having a single pin.

Turning now to FIG. 1, a testing device 10 in accordance with the invention is shown, including a proximal handle portion 12 having a generally flat distal face 14. The handle is cylindrical in the illustrated embodiment, but may be of any suitable shape (or size). Handle 12 is made of a plastic resin but may be made of any other appropriate material.

Figure 1A:
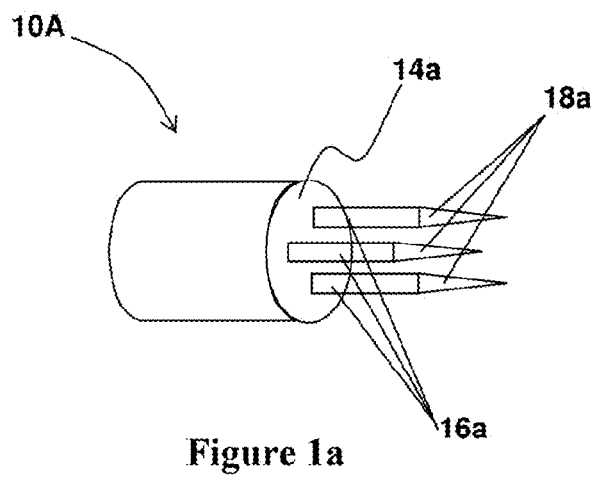
FIG. 1A is a perspective view of an alternate embodiment of the testing device of the invention having multiple pins.

A distally directed rigid wire or pin 16 is permanently mounted in handle 12 by conventional means and projects distally from surface 14. Preferably a single pin 16 is located along the central axis of the handle. However, in an alternate embodiment of the invention a plurality of distally directed wires or pins 16A may be used, preferably disposed in a regular pattern in bottom surface 14 as illustrated in FIG. 1A. Pin (or pins) 16 or 16A may have pointed tips 18 or 18A to facilitate insertion of the pins into the drywall to be tested, as discussed below.

Pins (or wires) 16 and 16A may be made of a metal that forms a visible tarnished layer or adhered scale when it reacts with sulfur or sulfur compounds, or with other corrosive materials. The pins therefore may be made of reactive metals that produce visible sulfides in the presence of such corrosive materials such as silver, copper or gold or alloys of silver, copper or gold. The pins may be made entirely of the reactive metal or they may be simply plated with the reactive metal. The use of solid or plated silver or sterling silver pins is currently preferred.

In an alternate embodiment, as illustrated in FIG. 2, one or more selected portions 20 of pin 16B may be made of one of the reactive metals or plated with the reactive metals so that these reactive portions are subject to visible oxidation or tarnishing in the presence of sulfur compounds or other corrosive materials and the remaining portions 22 of the pin may be made of (or plated with) a non-reactive metal which does not produce noticeable oxidation or tarnish. This helps establish a sharp demarcation between the tarnished and nontarnished areas thereby facilitating the testing method of the invention.

Figure 1B:
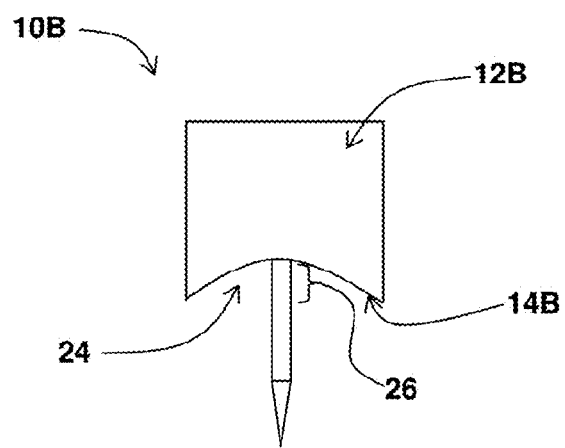
FIG. 1B is an elevation of an alternate embodiment of the testing device of the invention in the distal face of the handle is concave.

Such demarcation can also be established by forming a cavity 24 in a concave distal face 14B of handle 12B of testing device 10B of FIG. 1B. Since this configuration will prevent the entirety of the pin from entering the drywall, the portion 26 which does not enter the drywall when the handle is pressed against the drywall surface will corrode or tarnish far slower than the embedded portions, again establishing a demarcation that will aid the testing process.

FIG. 3 illustrates an alternative embodiment in which testing device 10C has a security seal 28 located at distal face 14C of handle 12C. The seal includes a frangible central member 30 permanently affixed to the distal face of the handle by an adhesive layer 32 located at the interface of the seal and distal face. A second adhesive layer 34 is provided on the distal surface of the frangible central member (or applied just before placing the device in the drywall). Preferably, adhesive layer 34 will have a protective liner 36 that will be removed before application of the device.

The frangible central member may be, for example, a piece of cardboard that will tear or separate when an installed testing device 10C is removed from its installed location. Thus, when the pin is pressed home against a gypsum board, layer 34 will adhere to the gypsum board. Then, when the testing device is removed from the gypsum board, adhesive layer 34 will remain attached to the surface of the drywall causing the seal to break apart in the frangible central member thereby providing a positive indication that the device was removed from its original location and preventing it from being replaced surreptitiously at a later time to give a false indication that no corrosive material was present.

The testing devices of the invention will be used as follows:

1. A plurality of suitable test locations on any drywall suspected to contain corrosive material (e.g., $H_2S$) will be chosen.

Figure 4:
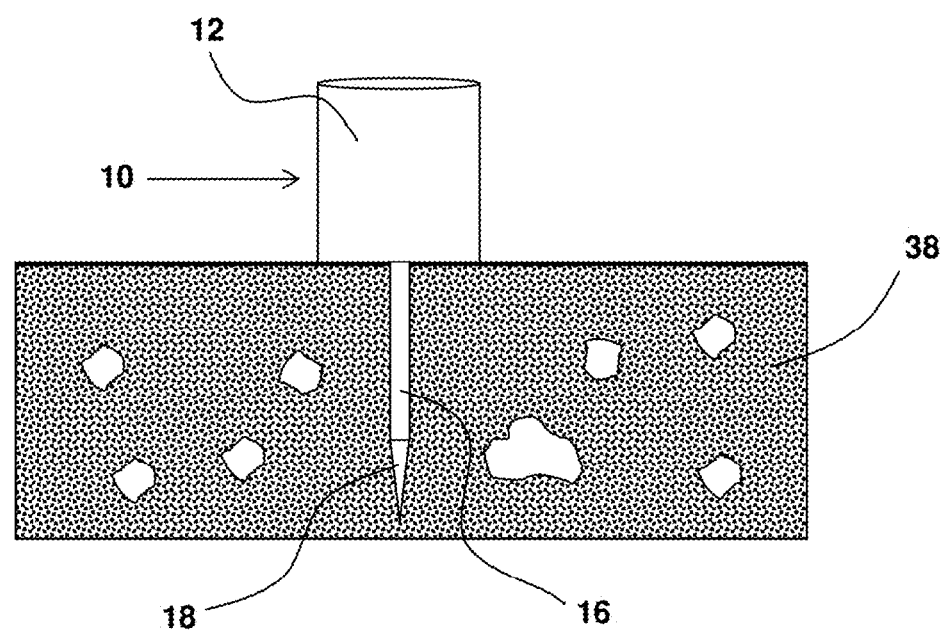
FIG. 4 is an elevation view of the testing device of FIG. 1 in place in a selected piece of drywall where the drywall is shown cut-away to highlight the location of the device.

2. A plurality of test devices 10, 10A, 10B, or 10C will be pressed into the test locations in the selected areas of drywall 38, as depicted in FIG. 4 for test device 10. Preferably the pins will be spaced about four feet apart or closer to obtain optimal spacing for testing individual sheets of drywall which are typically 4 feet wide and 8 to 12 feet long.

3. If test devices with a security seal are provided, the security seal will be prepared so that when the handle of the test device is pressed home into the drywall, the security seal will adhere to the outer surface of the drywall.

4. If desired, in an alternative approach, small holes may be created in the drywall using a rigid tool with the same dimensions as the wire or pin 16, 16A, 16B or 16C before emplacing the test devices. If test devices with wires rather than rigid pins are used, creating holes in the drywall will be required.

5. The testing devices will be left in place for a test period of time sufficient to detect corrosive materials. In the case of Chinese drywall and test devices with pins made of silver, it has been found that a period of about 5-7 days is sufficient.

6. After the test period, the pins will be removed, the locations from which they were removed noted, and the pins will be inspected. If a visible corrosion or tarnished layer is seen on some or all of the pins, the areas from which these pins were removed will be marked as tainted with the corrosive materials.

7. Appropriate steps will be taken to deal with the problematic drywall.

EXAMPLES

The following example further illustrates the invention but should not be construed as in any way limiting its scope.

A number of drywall installations were tested using testing devices in accordance with the present invention, where a single rigid and sharp tipped solid silver pin was used. Some of the samples were known to be Chinese drywall containing measurable levels of elemental sulfur at both higher and lower concentrations. The samples with higher concentrations of the elemental sulfur caused visible sulfide layers to be formed on the pins within two days after they were put in place. The drywall samples with lower levels of elemental sulfur took between five and seven days to produce visible sulfide layers on the pins. Domestic brands of gypsum drywall containing no elemental sulfur did not cause any visible sulfide layer to be formed even after 30 days.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method for detecting the presence of corrosive material in drywall having a gypsum core comprising:
   providing a testing device having a handle with a security seal affix to the distal face of the handle by frangible member and a pin projecting from the handle made of a metal that forms a visible layer or scale when it reacts with corrosive materials;
   pressing the pin into the core of the drywall to be tested and affixing the security seal to the surface of the drywall;
   leaving the pin in place a sufficient period to produce a visible layer indicative of the presence of a detectable amount of corrosive material; and
   removing and inspecting the pin to determine whether the visible layer indicative of the presence of corrosive material in the core is present.

2. The method of claim 1 in which a plurality of pins project from the handle.

3. The method of claim 1 in which the pin has a sharpened tip.

4. The method of claim 1 in which a wire instead of the pin projects from the handle, a hole for receiving the wire is formed in the drywall and the testing device is attached to the drywall with the wire positioned within the hole.

5. The method of claim 1 in which selected portions of the pin are made of or plated with reactive metals.

6. The method of claim 1 in which the distal face of the handle is convex establishing a portion which does not enter the drywall when the pin is pressed into the drywall.

7. The method of claim 1 in which the pin comprises a reactive material chosen from the group consisting of silver, copper, or gold, or alloys of silver, copper or gold.

8. The method of claim 7 in which the pin is comprised entirely of the reactive metal.

9. The method of claim 7 in which the pin is plated with the reactive metal.

10. The method of claim 1 in which the security seal includes a frangible central member affixed to the distal face of the handle.

11. The method of claim 10 in which an adhesive layer is provided on the distal surface of the frangible central member.

12. The method of claim 10 in which the frangible central member is made of cardboard which will tear or separate when the testing device is removed from its installed location.

13. A testing device for detecting the presence of corrosive material in drywall comprising:
    a handle with a pin projecting from the handle and a security seal affix to the distal face of the handle by frangible member, the pin being made of a metal that forms a visible layer or scale when it reacts with the corrosive materials.

14. The testing device of claim 13 in which a plurality of pins made of a metal that forms a visible layer or scale when it reacts with the corrosive materials project from the handle.

15. The testing device of claim 13 in which the pin comprises a reactive material chosen from the group consisting of silver, copper, or gold, or alloys of silver, copper or gold.

16. The testing device of claim 13 in which selected portions of the pin are made of or plated with reactive metals.

17. The testing device of claim 13 in which the distal face of the handle is convex to establish a pin portion that does not enter the drywall when the pin is pressed into the drywall.

18. The testing device of claim 13 in which the security seal includes a frangible central member affixed to the distal face of the handle and an adhesive layer on the distal surface of the frangible central member.

* * * * *